United States Patent [19]

Crivello

[11] 4,219,654

[45] Aug. 26, 1980

[54] PHOTOINITIATORS

[75] Inventor: James V. Crivello, Elnora, N.Y.

[73] Assignee: General Electric Company, Schenectady, N.Y.

[21] Appl. No.: 949,642

[22] Filed: Oct. 10, 1978

Related U.S. Application Data

[60] Division of Ser. No. 789,419, Apr. 21, 1977, Pat. No. 4,136,102, which is a division of Ser. No. 574,006, May 2, 1975, Pat. No. 3,981,897, which is a continuation-in-part of Ser. No. 466,374, May 2, 1974, abandoned, Ser. No. 466,375, May 2, 1974, abandoned, and Ser. No. 466,378, May 2, 1974, abandoned.

[51] Int. Cl.$^2$ .......................................... C07D 213/48
[52] U.S. Cl. ........................................ 546/342; 546/2; 546/8; 546/9; 546/174; 260/239 R; 260/440; 260/446; 260/439 R; 260/429 R; 549/3; 549/78; 568/8; 568/13; 568/16; 260/550
[58] Field of Search ........................................ 546/342

[56] References Cited

U.S. PATENT DOCUMENTS

| | | | |
|---|---|---|---|
| 4,056,532 | 11/1977 | Connor et al. | 546/342 |
| 4,150,233 | 4/1979 | Chadwick | 546/332 |

FOREIGN PATENT DOCUMENTS

| | | | |
|---|---|---|---|
| 568187 | 6/1958 | Belgium | 546/342 |
| 1137020 | 12/1968 | United Kingdom | 546/342 |

*Primary Examiner*—Donald G. Daus
*Assistant Examiner*—James H. Turnipseed
*Attorney, Agent, or Firm*—William A. Teoli; James C. Davis, Jr.

[57] ABSTRACT

Halogen onium salts, and onium salts of Group VA and VIA elements having an $MF_6^-$ anion, where M is selected from P, As and Sb, have been found to exhibit unusual activity under ultraviolet light. These onium salts can be employed as cationic photoinitiators when used with a variety of organic resins and cyclic organic compounds.

1 Claim, No Drawings

PHOTOINITIATORS

This application is a division of Ser. No. 789,419, filed Apr. 21, 1977, now U.S. Pat. No. 4,136,102, which is a division of copending application Ser. No. 574,006, filed May 2, 1975, now U.S. Pat. No. 3,981,897 which is a continuation-in-part of copending applications Ser. No. 466,374, abandoned Ser. No. 466,375 abandoned and Ser. No. 466,378 filed concurrently on May 2, 1974 now abandoned and assigned to the same assignee as the present invention.

The present invention relates to onium salt photoinitiators of halogen, Group Va and VIa elements having an $MF_6^-$ anion, where M is an element selected from P, As and Sb.

The photoinitiator compositions of the present invention can be used in combination with various organic resins, such as epoxy resins, to produce UV curable compositions. The photoinitiators of the present invention are included by the formula $$Y^+(MF_6)^- \quad (1)$$

where M is an element selected from P, As and Sb, and Y is a cation selected from $$[(R)_a(R^1)_b Q]^{+},$$
$$[(R)_c(R^2)_d(R^3)_e X]^{+},$$
$$[(R)_f(R^4)_g(R^5)_h Z]^{+},$$

where R is a monovalent aromatic organic radical, $R^1$ is a divalent aromatic organic radical, $R^2$ is a monovalent organic aliphatic radical selected from alkyl, cycloalkyl and substituted alkyl, $R^3$ is a polyvalent organic radical forming a heterocyclic or fused ring structure selected from aliphatic radicals and aromatic radicals, $R^4$ is a monovalent organic aliphatic radical selected from alkyl, alkoxy, cycloalkyl and substituted derivatives thereof, $R^5$ is a polyvalent organic radical forming an aromatic heterocyclic or fused ring structure with Z, Q is a halogen radical such as I, Br, Cl, etc., X is a Group VIa element selected from sulfur, selenium and tellurium, Z is a Group Va element selected from N, P, As, Sb and Bi, a is a whole number equal to 0 or 2, b is a whole number equal to 0 or 1, the sum of a+b is equal to 2 or the valence of Q, c is a whole number equal to 0 or 3, d is a whole number equal to 0 to 2 inclusive, e is a whole number equal to 0 or 1, where the sum of c+d+e is a value equal to 3 or the valence of X, f is a whole number equal to 0 to 4 inclusive, g is a whole number equal to 0 to 2 inclusive, and h is a whole number equal to 0 to 2 inclusive, and the sum of f+g+h is a value equal to 4 or the valence of Z.

Radicals included by R can be the same or different, aromatic carbocyclic or heterocyclic radical having from 6 to 20 carbon atoms, which can be substituted with from 1 to 4 monovalent radicals selected from $C_{(1-8)}$ alkoxy, $C_{(1-8)}$ alkyl, nitro, chloro, etc., R is more particularly phenyl, chlorophenyl, nitrophenyl, methoxyphenyl, pyridyl, etc. Radicals included by $R^1$ are divalent radicals such as

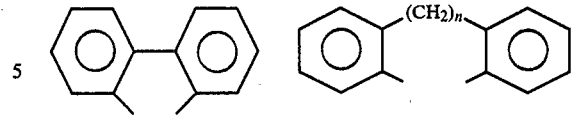

$R^2$ radicals include $C_{(1-8)}$ alkyl such as methyl, ethyl, etc., substituted alkyl such as $-C_2H_4OCH_3$, $-CH_2COOC_2H_5$, $-CH_2COCH_3$, etc. $R^3$ radicals include such structures as:

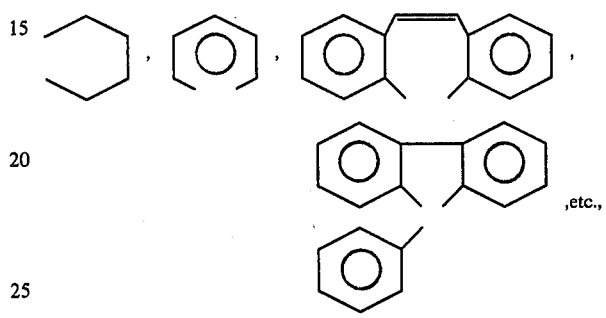

$R^4$ radicals include $C_{(1-8)}$ alkyl, $C_{(3-8)}$ cycloalkyl, substituted alkyl such as haloalkyl, for example, chloroethyl; alkoxy such as $OCH_2C_6H_5$ and $OCH_3$; alkoxyalkyl such as $-C_2H_4OCH_3$, etc. Radicals included by $R^5$ are, for example,

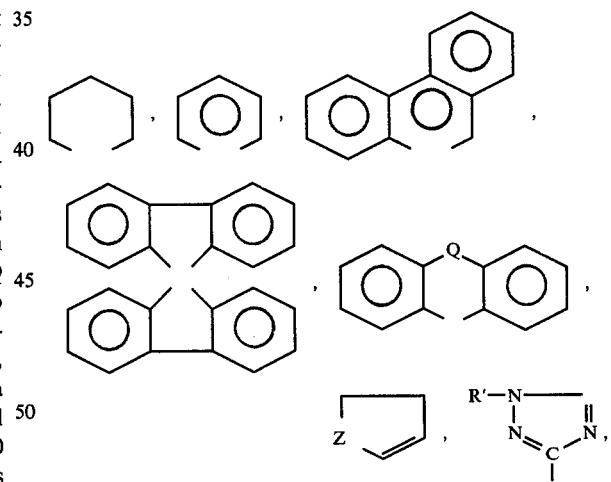

where Q' is selected from O, $CH_2$, N, R and S; Z is selected from —O—, —S— and $$\overset{R'}{\underset{|}{-N-}},$$

and R' is a monovalent radical selected from hydrogen and hydrocarbon.

Halonium salts included by Formula 1 are, for example,

-continued

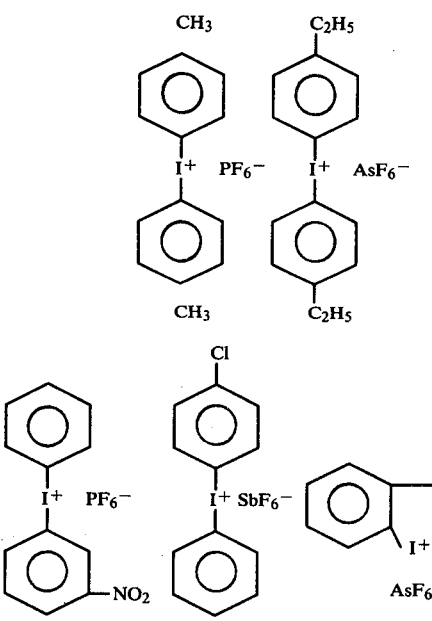

Group VIa onium salts included by Formula 1 are, for example,

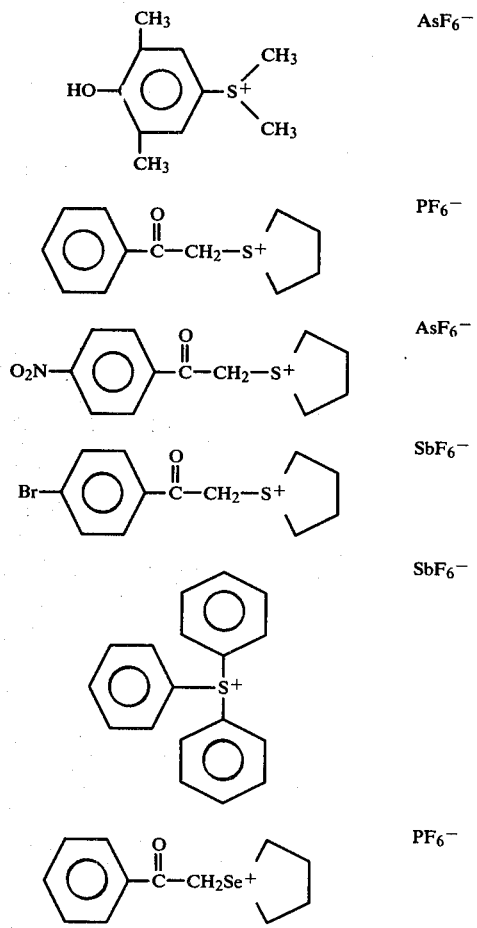

-continued

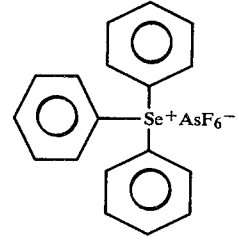

SbF$_6^-$, etc.

Group Va onium salts included by Formula 1 are, for example,

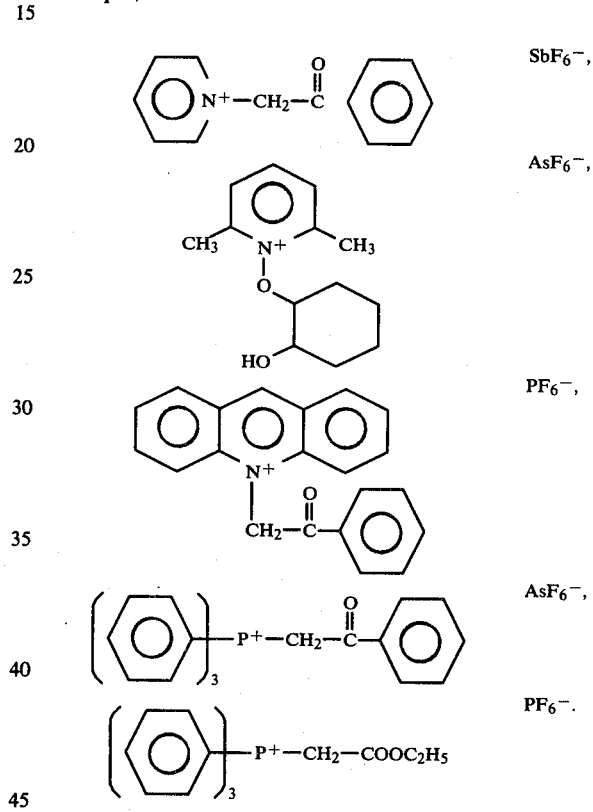

As shown in my copending application Ser. No. 574,007 filed May 2, 1975, now U.S. Pat. No. 3,981,892 and assigned to the same assignee as the present invention, where Y in Formula 1 contains a Q radical, the photoinitiator can be made by effecting contact under aqueous conditions between an arylhalonium bisulfate and the corresponding hexafluoro acid or salt, such as Y$^1$M F$_6$, where Y$^1$ can be hydrogen, an alkali metal ion, alkaline earth metal ion or transition metal ion.

In addition to the above-described metathesis for making the corresponding halonium salts, the halonium salts of the present invention, also can be prepared by using silver compounds, such as silver oxide, or silver tetrafluoroborate, which were reacted with the appropriate diarylhalonium salt, as shown by M. C. Caserio et al., J. Am. Chem. Soc. 81, 336 (1959) or M. C. Beringer et al., J. Am. Chem. Soc. 81, 342 (1959). Methods for making Group VIa compounds, such as sulfonium, selenium and tellurium compounds, where Y of Formula 1 contains an X radical can be made by procedures shown in J. W. Knapczyk and W. E. McEwen, J. Am. Chem. Soc., 91 145, (1969); A. L. Maycock and G. A.

Berchtold, J. Org. Chem., 35 No. 8, 2532 (1970); H. M. Pitt, U.S. Pat. No. 2,807,648, E. Goethals and P. De Radzetzky, Bul. Soc. Chim. Belg., 73 546 (1964); H. M. Leichester and F. W. Bergstrom, J. Am. Chem. Soc., 51 3587 (1929), etc.

Among the procedures which can be used to make Group Va onium salts, arsonium, antimonium and bimuthonium salt, where Y in Formula 1 is a Z radical can be found in Goerdeler, Methoden der Organishen Chemie 11/2, 591-640 (1958) and K. Sasse, idid, 12/1 79-112 (1963).

The following examples are given by way of illustration and not by way of limitation. All parts are by weight.

EXAMPLE 1

There was added a cooled solution of about 100 ml of acetic acid and 70 ml of concentrated sulfuric acid to a suspension of 100 g of potassium iodate in 100 ml of acetic anhydride and 90 ml of benzene. During the addition, the mixture was stirred and maintained below 5° C. When the addition was complete, the reaction mixture was allowed to warm to room temperature and stirred for 48 hours. There was then added 400 ml of distilled water. The aqueous portion of the reaction mixture was extracted three times with diethyl ether and petroleum ether to remove unreacted organic materials. A pale yellow crystalline product formed upon addition of ammonium chloride to the aqueous reaction mixture. There was obtained a 48% yield of diphenyliodonium chloride having a m.p. of 180°-185° C. After recrystallization, the pure salt had a m.p. of 228°-229° C.

A photoinitiator was prepared within the scope of Formula 1, having a Q containing Y cation as follows:

A mixture of 20 g of moist, freshly prepared $Ag_2O$, 10 ml of water and 31.7 g of diphenyliodonium chloride was ground together in a slurry. The wet mixture was filtered and washed with water to produce 360 ml of filtrate. The filtrate was cooled until a substantial amount of the solution had frozen. There was slowly added 25 ml 45-50% $HBF_4$ cooled to $-15°$ C. The cold solution was stirred and allowed to warm to room temperature. A white crystalline solid separated and was collected by filtration. There was obtained a 60% yield of diphenyliodonium fluoroborate, m.p. 136° C. when the solid was dried overnight in vacuo at 60° C.

Replacement in the above procedure of $HBF_4$ with $HPF_6$ and $HSbF_6$, yielded the corresponding diphenyliodonium hexafluorophosphate mp. 138°-141° C., and diphenyliodonium hexafluoroantimonate mp 58°-57° C.

The salts were dissolved in acetonitrile (3 g salt to 10 ml acetonitrile) and then added to 4-vinylcyclohexene dioxide such that there was present 3% by weight of the salt. The solutions were coated as 3 mil films onto glass slides and exposed to UV irradiation from a GE H3T7 lamp at a distance of 6 inches. The minimum time required to produce a tack-free film was recorded as the cure time. By tack free is meant that the film was no longer tacky and an imprint was not left when a thumb was impressed on its surface.

Under these conditions, the following results were recorded:

| Salt | | Cure Time (sec.) |
|---|---|---|
| $(C_6H_5)_2I^+$ | $BF_4^-$ | 30 |
| " | $PF_6^-$ | 20 |
| " | $SbF_6^-$ | 3-5 |

Clearly, those salts possessing the $MF_6^-$ anion were much faster than the salts having the $BF_4^-$ anion.

EXAMPLE 2

A solution of about 200 parts of sulfuric acid in about 300 parts of acetic acid was added at a temperature between 0° to 3° C. to a mixture, while it was being agitated, of 200 parts of potassium iodate, about 300 parts of toluene, about 900 parts of acetic acid, and about 400 parts of acetic anhydride. The mixture was then stirred for 11 hours after all of the sulfuric acid and the acetic acid had been added. The resulting inorganic salts were removed by filtration and then washed with a small amount of cold glacial acetic acid. A pale yellow solution was obtained which was diluted to twice its volume with water and extracted three times with ether. A small amount (0.3 part) of sodium sulfide was added as a reducing agent.

Based on method of preparation, there was obtained a quantitative yield of 4,4'-dimethyldiphenyliodonium bisulfate. A slightly warm solution of substantially equal molar amounts of 4,4'-dimethyldiphenyliodonium bisulfate and potassium hexafluoroarsenate was allowed to cool. There was obtained a white crystalline deposit. The product was filtered and washed with distilled water. A second crop of crystals was obtained on further standing. After the crystals were dried overnight, there was obtained 27 parts of a product having a melting point of 148°-152° C. Recrystallization of the product from a water ethanol mixture resulted in a product having a melting point of 163°-166° C. Based on method of preparation and NMR spectra and elemental analysis for $C_{14}H_{14}IAsF_6$ calculated: percent C, 33.74; percent H, 2.81; percent As, 15.06, found: percent C, 33.70; percent H, 2.92; percent As, 15.28, the product was 4,4'-dimethyldiphenyliodonium hexafluoroarsenate.

By a similar procedure, treatment of 4,4'-dimethyldiphenyliodonium bisulfate with $KSbF_6$ and $KPF_6$ resulted in 4,4'-dimethyldiphenyliodonium hexafluoroantimonate m.p. 75°-80° C. and 4,4'-dimethyldiphenyliodonium hexafluorophosphate mp 169°-172° C.

4,4-dimethyldiphenyliodonium tetrafluoroborate was prepared by treatment of the 4,4'-dimethyldiphenyliodonium bisulfate with ammonium chloride in water and isolating the resulting 4,4'-dimethyldiphenyliodonium chloride. The dry chloride salt (34.5 g) was slurried together with 20 g freshly prepared silver oxide and 10 ml water. The mixture was then filtered and washed to produce 360 ml filtrate. The filtrate was cooled until nearly the entire solution had been frozen, and then a cold solution of 25 ml 45-50% $HBF_4$ was added. The mixture was stirred and slowly allowed to warm to room temperature. The white crystalline product which separated was 4,4'-dimethyldiphenyliodonium fluoroborate mp 95°-100° C.

A comparative study of the cure ratio was performed on 3% of each of the salts dissolved directly in 4-vinylcyclohexene dioxide, as described in Example 1. The results obtained were as follows:

| Salt | | Cure Time (sec.) |
|---|---|---|
| [CH₃–⌬–]₂I⁺ | BF₄⁻ | 60 |
| " | PF₆⁻ | 20 |
| " | AsF₆⁻ | 5 |
| " | SbF₆⁻ | 3 |

The above results show that the MF₆⁻ salts provided unexpected results over the prior art BF₄⁻ salt.

EXAMPLE 3

Triphenylselenonium chloride was prepared according to the procedure of H. M. Leicester and F. W. Bergstrom, J. Am. Chem. Soc., 51 3587 (1929) starting with diphenyl selenide. The corresponding fluoroborate, hexafluoroarsenate and hexafluoroantimonate salts were prepared by adding sodium hexafluoroarsenate, sodium tetrafluoroborate or potassium hexafluoroantimonate to an aqueous solution of triphenylselenonium chloride. The products which contained Y radicals as shown in Formula 1, where Y was an X containing cation, were white crystalline solids which were dried in vacuo.

Three percent solutions of the above salts in 4-vinylcyclohexene dioxide were cured as 2 mil films at a distance of six inches from a GE H3T7 lamp. The following cure times were observed:

| Salt | Cure Time |
|---|---|
| $(C_6H_5)_3Se^+BF_4^-$ | 10 sec. |
| $(C_6H_5)_3Se^+AsF_6^-$ | 5 sec. |
| $(C_6H_5)_3Se^+SbF_6^-$ | 3 sec. |

The above results show that the hexafluoro salt is a superior photosensitizer with respect to cure time as compared to the tetrafluoroborate salt.

EXAMPLE 4

Additional curable compositions were prepared using the epoxy resin mixture of Example 1 and a variety of phosphonium salts as shown as follows where cation is the organic portion corresponding to Y of Formula 1, where Y contains a Z radical, anion is the Lewis Acid portion, m.p. is the melting point of the crystalline onium salt and "cure time" is as previously defined.

| | Cation | Anion | m.p.(°C.) | Cure Time (min.) |
|---|---|---|---|---|
| I | $(C_6H_5)_4P^+$ | BF₄⁻ | 350 | 9 |
| II | $(C_6H_5)_3P^+-CH_3$ | BF₄⁻ | 125–127 | 10 |
| III | $(C_6H_5)_3P^+-CH_2-C(=O)-C_6H_5$ | SbF₆⁻ | 149–152 | 1 |
| IV | $(C_6H_5)_3P^+-CH_2-C(=O)-C_6H_5$ | AsF₆⁻ | 194–197 | 1 |
| V | $(C_6H_5)_3P^+-CH_2-C(=O)-C_6H_5$ | PF₆⁻ | 203–206 | 1 |
| VI | $(C_6H_5)_3P^+$–(biphenyl) | BF₄⁻ | 297–302 | 5 |

-continued

| Cation | | Anion | m.p.(°C.) | Cure Time (min.) |
|---|---|---|---|---|
| VII | (phosphonium cation with dihydroxyphenyl and three phenyl groups) | BF$_4^-$ | 260 | 1.5 |
| VIII | (phosphonium cation with dihydroxynaphthyl and three phenyl groups) | BF$_4^-$ | 258–263 | 1 |

EXAMPLE 5

In accordance with the procedure of Example 1, additional iodonium salts were prepared as shown by the following table, where

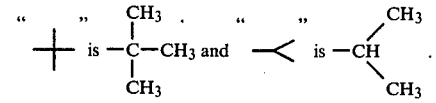

"$+$" is $-\underset{\underset{CH_3}{|}}{\overset{\overset{CH_3}{|}}{C}}-CH_3$ and "$\prec$" is $-\underset{CH_3}{\overset{CH_3}{CH}}$

IODONIUM SALTS

| Cation Structure | Anion | M.P. (°C.) | λMax (εMax) | | Elemental Analysis | | | |
|---|---|---|---|---|---|---|---|---|
| (t-Bu)-C$_6$H$_4$-I$^+$-C$_6$H$_4$-(t-Bu) | PF$_6^-$ | 173–174 | 238(20,000) | calc: found: | C 44.61 45.13 | H 4.33 5.25 | I 5.76 5.07 | |
| (t-Bu)-C$_6$H$_4$-I$^+$-C$_6$H$_4$-(t-Bu) | AsF$_6^-$ | 169–171 | 238(20,700) | calc: found: | C 41.24 41.28 | H 4.47 4.46 | As 12.89 12.70 | |
| (t-Bu)-C$_6$H$_4$-I$^+$-C$_6$H$_4$-(t-Bu) | SbF$_6^-$ | 163–175 | 238(21,200) | calc: found: | C 38.16 37.91 | H 4.13 4.14 | I 20.19 19.90 | Sb 19.20 19.10 |
| (i-Pr)-C$_6$H$_4$-I$^+$-C$_6$H$_4$-(i-Pr) | PF$_6^-$ | — | 238(17,700) | calc: found: | C 42.35 | H 4.31 | I 24.9 | P 6.08 |
| (i-Pr)-C$_6$H$_4$-I$^+$-C$_6$H$_4$-(i-Pr) | AsF$_6^-$ | 156–157 | 238(19,900) | calc: found: | C 38.99 38.92 | H 3.97 3.85 | I 22.92 23.01 | As 13.54 13.62 |
| Cl-C$_6$H$_4$-I$^+$-C$_6$H$_4$-Cl | AsF$_6^-$ | 194–195 | 240(23,600) | calc: found: | C 26.72 26.85 | H 1.48 1.59 | As 13.91 13.72 | |
| Br-C$_6$H$_4$-I$^+$-C$_6$H$_4$-Br | AsF$_6^-$ | 214–215 | 240(31,600) | calc: found: | C 22.93 23.15 | H 1.27 1.33 | | |
| CH$_3$-C(O)-NH-C$_6$H$_4$-I$^+$-C$_6$H$_4$-NH-C(O)-CH$_3$ | AsF$_6^-$ | 232–234 | 275(30,600) | calc: found: | C 32.8 33.00 | N 4.80 4.87 | H 2.74 2.79 | I 21.7 21.9 |
| (diphenyleneiodonium) | AsF$_6^-$ | 268–270 | 264(17,300) | calc: found: | C 30.77 30.85 | H 1.71 1.70 | I 27.14 26.80 | As 16.03 16.20 |
| C$_2$H$_5$-C$_6$H$_4$-I$^+$-C$_6$H$_4$-C$_2$H$_5$ | AsF$_6^-$ | 104–105 | — | | — | — | — | — |
| O$_2$N-C$_6$H$_4$-I$^+$-C$_6$H$_4$-NO$_2$ | AsF$_6^-$ | 192–195 | 215(35,000) 245(17,000) | calc: found: | C 25.9 26.0 | H 1.43 1.42 | I 5.0 5.05 | 22.6 22.8 |

The above halonium salts were found to exhibit substantially the same utility with respect to a faster rate of cure of 4-vinylcyclohexene dioxide as compared to prior art photoinitiators as shown for Example 1.

EXAMPLE 6

Several sulfonium hexafluoroarsonium salts, sulfonium hexafluoroantimonate salts and selenium hexafluoroarsonium salts, where Y in Formula 1 is an X containing cation, were prepared by adding the corresponding anion in the form of the acid or salt, such as sodium hexafluoroarsenate to the corresponding cation structure, such as an aqueous solution of tri(3,5-dimethyl-4-hydroxy)phenyl sulfonium chloride. The procedure described by H. M. Leicester and F. W. Bergstrom, J. Am. Chem. Soc. 51 3587 (1929) was employed. The following table shows the results obtained.

It was found that 4-vinylcyclohexene dioxide compositions containing the above onium salts exhibited a faster rate of cure, as compared to comparable prior art tetrafluoroborate anium salts.

EXAMPLE 7

In addition to the aforementioned halonium salt and sulfonium salts falling within the scope of Formula 1, where Y is a Q containing and X containing cation, several phosphonium salts and ammonium salts were prepared by the procedure shown by J. Goerdeler, Methoden der Organishen Chimie, 1/12 591–640 (1958). The latter onium salts, where Y in Formula 1 is a cation containing a Z radical are shown as follows:

| Cation Structures | SULFONIUM SALTS Anion | M.P. (°C.) | λMax (εMax) | Elemental Analysis | | | |
|---|---|---|---|---|---|---|---|
| (3,5-dimethyl-4-hydroxyphenyl)dimethylsulfonium | $AsF_6^-$ | 154-156 | 300(3,000) 284(4,100) 279(4,600) 252(9,300) | calc: found: | C 33.20 32.99 | H 4.15 3.90 | S 8.75 8.92 |
| tris(3,5-dimethyl-4-hydroxyphenyl)sulfonium | $AsF_6^-$ | 245-251 | 263(23,300) 280(20,708) 317(7,150) | calc: found: | C 49.3 49.39 | H 4.62 4.59 | S 5.48 5.55 |
| triphenylselenonium | $AsF_6^-$ | 184-187 | 258(10,900) 266(2,841) 275(2,145) | calc: found: | C 43.3 43.4 | H 3.01 2.99 | Se 15.8 16.0 |
| triphenylselenonium | $SbF_6^-$ | 140-143 | 258(10,900) 266(2,841) 275(2,145) | calc: found: | C 39.6 39.9 | H 2.75 2.98 | |
| phenacyltetrahydrothiophenium | $PF_6^-$ | 117-120 | 300(4,700) 248(10,200) | | | | |
| " | $AsF_6^-$ | 161-163 | 300(4,700) 248(10,200) | | | | |
| " | $SbF_6^-$ | 160-163 | 300(4,700) 248(10,200) | | | | |

| Cation Structure | PHOSPHONIUM SALTS Anion | M.P. (°C.) | λMax (εMax) | Elemental Analysis | | | |
|---|---|---|---|---|---|---|---|
| triphenyl(phenacyl)phosphonium | $PF_6^-$ | 203-206 | 313(2,900) | calc: found: | C 59.3 59.50 | H 4.2 4.10 | P 11.8 11.63 |
| " | $AsF_6^-$ | 194-197 | " | calc: found: | C 54.7 54.92 | H 3.86 3.03 | P 5.4 5.24 |
| " | $SbF_6^-$ | 149-152 | " | calc: found: | C 50.8 50.74 | H 3.6 3.70 | P 5.03 5.10 |

AMMONIUM SALTS

| Cation Structure | Anion | M.P. (°C.) | λMax (εMax) | Elemental Analysis | | | |
|---|---|---|---|---|---|---|---|
| | | | | | C | H | N |
| C$_6$H$_5$—N$^+$—CH$_2$CoC$_6$H$_5$ | PF$_6^-$ | 197–203 | 249(18,400) | calc: | 45.5 | 3.50 | 4.07 |
| | | | | found: | 45.63 | 3.57 | 4.10 |
| | | | | | C | H | N |
| " | AsF$_6^-$ | 202–205 | " | calc: | 40.3 | 3.1 | 3.61 |
| | | | | found: | 41.35 | 3.10 | 3.62 |
| | | | | | C | H | N |
| " | SbF$_6^-$ | 166–174 | " | calc: | 35.9 | 2.76 | 3.2 |
| | | | | found: | 35.9 | 3.00 | 3.1 |

In addition to using the photoinitiators of the present invention for curing epoxy resins, these onium salts of halogen, Group Va and VIa elements can be used to polymerize a variety of cyclic organic compounds and cyclic organosilicon compounds as shown in my copending applications Ser. Nos. 466,373, 466,376 and 466,377 filed May 2, 1974 now abandoned and assigned to the same assignee as the present invention.

What I claim as new and desire to secure by Letters Patent of the United States is:

1. The compound

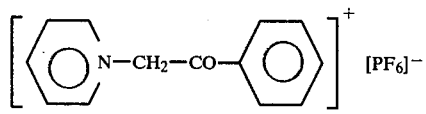

* * * * *